United States Patent
Dahl et al.

[11] 4,052,447
[45] Oct. 4, 1977

[54] PROCESS FOR THE PREPARATION OF BICYCLOALKANE DERIVATIVES

[75] Inventors: Helmut Dahl; Hans Peter Lorenz, both of Berlin, Germany

[73] Assignee: Schering Aktiengesellschaft, Berlin & Bergkamen, Germany

[21] Appl. No.: 641,998

[22] Filed: Dec. 18, 1975

Related U.S. Application Data

[63] Continuation of Ser. No. 461,279, April 16, 1974, abandoned.

[30] Foreign Application Priority Data

Apr. 18, 1973 Germany .............................. 2320285
Feb. 25, 1974 Germany .............................. 2409597

[51] Int. Cl.$^2$ ............................................. C07C 51/36
[52] U.S. Cl. .................... 260/514 G; 260/340.5 AS; 260/340.7; 260/340.9 AS; 560/256
[58] Field of Search ............................. 260/514 G, 491

[56] References Cited

U.S. PATENT DOCUMENTS 3,897,460   7/1975   Hajos .................. 260/340.9

FOREIGN PATENT DOCUMENTS 81,251   7/1963   France .................. 260/514

*Primary Examiner*—Robert Gerstl
*Attorney, Agent, or Firm*—Millen & White

[57] ABSTRACT

Bicycloalkanes of the formula

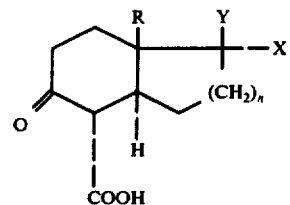

wherein $n$ is the integer 1 or 2; R is methyl or ethyl, and X and Y collectively are a free or ketalized oxo group or X is a hydrogen atom and y is a free, etherified or esterified hydroxy group, are produced by hydrogenating a compound of the formula

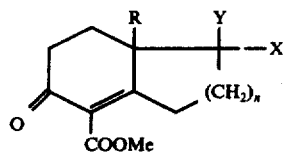

wherein $n$, R, X, and Y have the values given above and Me is an alkali metal atom, in an aqueous solution with hydrogen and a palladium-, platinum- or rhodium-containing hydrogenation catalyst. The corresponding free acid is obtained by acidifying the reaction mixture and isolating the reaction product.

6 Claims, No Drawings

PROCESS FOR THE PREPARATION OF BICYCLOALKANE DERIVATIVES

This is a continuation of application Ser. No. 461,279, filed Apr. 16, 1974 now abandoned.

This problem is solved, surprisingly, by the use of the alkali metal salts of the free acids, rather than the free acids, as starting compounds, and by conducting the hydrogenation in an aqueous solution.

SUMMARY OF THE INVENTION

According to this invention, alkali metal salts of bicycloalkanes of the general Formula I

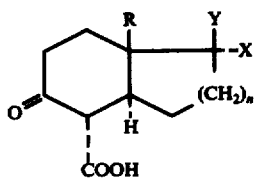

wherein n is the integer 1 or 2; R is methyl or ethyl, and X and Y collectively are a free or ketalized oxo group, or X is a hydrogen atom and Y is a free, etherified or esterified hydroxy group, are produced by hydrogenating a compound of general Formula II

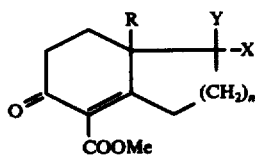

wherein n, R, X, and Y have the values given above and Me is an alkali metal atom, in an aqueous solution with hydrogen and a palladium-, platinum- or rhodium-containing hydrogenation catalyst. The corresponding free acid is obtained by acidifying the reaction mixture and isolating the reaction product.

DETAILED DISCUSSION

As will be apparent to one skilled in the art, the operability of the process and the utility of the hydrogenation product is not dependent upon the exact nature of the alkylenedioxy, alkoxy or acyloxy group, when present, as evidenced by the fact that these are merely functional derivatives of oxo (X, Y) and hydroxy (Y) groups, respectively, which can be present. Conversely, nothing is gained by employing a starting compound, one having an alkylenedioxy, alkoxy or acyloxy group which is complicated or high molecular weight.

Thus, when X and Y are a ketalized oxo group, the group is a conventional simple alkylenedioxy or phenylenedioxy ketalized oxo group, but other more complicated functionally equivalent ketalizing groups can be employed, if desired. Similarly, when Y is an etherified or esterified hydroxy group, the group is a conventional simple alkoxy or acyloxy group, but here also, more complicated functionally equivalent alkoxy and acyloxy groups can be employed, if desired.

Thus, when X and Y are alkylenedioxy, the group preferably is lower-alkylenedioxy, viz., one whose alkylene moiety is of 2-6 carbon atoms, preferably with 2-3 bridging carbon atoms. Examples of such alkylenedioxy are: ethylenedioxy, 1,3-propylenedioxy, 2,2-dimethylpropylenedioxy, 2,3-butylenedioxy and 3,4-hexylenedioxy.

When Y is alkoxy, the group is preferably loweralkoxy, i.e., wherein alkyl group is of 1-6 carbon atoms. Examples of alkoxy are: methoxy, ethoxy, propoxy, isopropoxy, butoxy and tert.-butoxy group.

When Y is acyloxy, the group is preferably one wherein the acyl radical is that of a lower carboxylic acid, i.e., of 1-8 carbon atoms, preferably a hydrocarbon carboxylic acid. Examples of such acyloxy groups are formyloxy, acetoxy, propionyloxy, dimethylacetoxy, trimethylacetoxy, butyryloxy, tert.-butylacetoxy, hexanoyloxy, benzoyloxy.

Other examples of acyloxy are cycloalkanoyloxy, cycloalkylalkanoyloxy, aroyloxy, alkaryloxy and aralkanoyloxy groups, e.g., cyclohexylcarboxy, cyclopentylacetoxy, p-methylbenzoyloxy and phenylacetoxy.

As will be apparent, the alkylenedioxy, phenylenedioxy, alkoxy and acyloxy groups can bear one or more simple, non-interfering substituents.

Examples of starting compounds for the process of this invention, in addition to those of the Examples hereinafter, are the respective sodium salts of 1,β-tert.-butoxy-5-oxo-7aβ-ethyl-5,6,7,7a-tetrahydroindan-4-carboxylic acid, 1β-hydroxy-5-oxo-7aβ-ethyl-5,6,7,7a-tetrahydroindan-4-carboxylic acid, 1β-acetoxy-5-oxo-7a⊕-ethyl-5,6,7,7a-tetrahydroindan-4-carboxylic acid, 1,5-dioxo-7aβ-ethyl-5,6,7,7a-tetrahydroindan-4-carboxylic acid, 1-ethylene-dioxy-5-oxo-7aβ-methyl-5,6,7,7a-tetrahydroindan-4-carboxylic acid, 1-phenylenedioxy-5-oxo-7aβ-methyl-5,6,7,7a-tetra-hydroindan-4-carboxylic acid, and 1β-acetoxy-5-oxo-7aβ-methyl-5,6,7,7a-tetrahydroindan-4-carboxylic acid, the corresponding potassium salts and the corresponding sodium or potassium salts of 8a-methyl(or ethyl)-1,6-dioxo-2,3,4,7,8,8a-hexahydronaphthalene-5-carboxylic acid and 1β-hydroxy-8a-methyl(or ethyl)-6-oxo-2,3,4,7,8,8a-hexahydronaphthalene-5-carboxylic acid and the functional derivatives thereof.

The process of this invention is effected using a conventional palladium-, platinum-, or rhodium-containing hydrogenation catalyst. Examples of such hydrogenation catalysts are the following: 5 or 10% palladium—animal charcoal catalyst; 10% palladium—barium sulfate catalyst; 5 or 10% palladium—calcium carbonate catalyst; platinum black catalyst; Adam's catalyst (platinum(IV) oxide); 5 or 10% rhodium—charcoal catalyst; and 5 or 10% rhodium—aluminum oxide catalyst.

The process of this invention is conducted with an aqueous solution of an alkali metal salt of general Formula I. These solutions are preferably prepared by combining the corresponding free acids in an aqueous medium with 0.9-1.1 equivalents of the corresponding bases. Examples of suitable bases are: aqueous solutions of sodium or potassium hydroxide. Basically, it is possible to employ aqueous solutions containing a water-soluble inert organic solvent conventionally employed in low pressure hydrogenations, such as, for example, methanol, ethanol, isopropanol, glycol monomethyl ether, dioxane, tetrahydrofuran, or dimethylformamide. However, such organic solvents have the disadvantage that the working up of the reaction mixtures is generally more difficult.

The process can be conducted employing a dilute or concentrated solution of the starting compound of Formula II, e.g., 80-250 g./l. The pH is that required to maintain the starting compound predominantly and preferably completely as an alkali metal, preferably pH = 5 or higher.

The hydrogenation can be accomplished at room temperature, as well as at a lower or higher temperature. A reaction temperature of 0° to +50° C. is preferably employed.

The hydrogenation can be effected under normal pressure as well as elevated pressure. The hydrogenation is preferably conducted at a hydrogen pressure of 1–50 atmospheres.

After the hydrogenation has been completed, the reaction mixture is acidified to liberate the free acid and worked up in the usual manner. For the acidification of the mixture, dilute mineral acids are suitably employed, such as, for example, hydrochloric acid, sulfuric acid, or phosphoric acid. Subsequently, the mixture can be extracted with a water-immiscible solvent, such as, for example, with methylene chloride, chloroform, ethyl acetate, or diethyl ether, and the extract can be worked up as usual.

The compounds of general Formula I are, as is known, valuable intermediates which are preferably utilized for the total synthesis of steroids. These active steroid compounds are produced e.g., by processes as described in Germany Laid-Open Applications DOS Nos. 1,949,793 and 1,950,012.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

These examples illustrate both the conductance and superiority of the process of this invention. To illustrate such superiority, compounds of general Formula I were produced, respectively, under the conditions of the process of this invention and under the conditions of the published process. The thus-obtained crude hydrogenation products were analyzed by means of gas chromatography on a column impregnated with diethyl glycol adipate.

The unknown starting products are prepared from the known 1$\beta$-tert.-butoxy-5-oxo-7a$\beta$-methyl-5,6,7,7a-tetrahydroindan-4-carboxylic acid by splitting off the 1$\beta$-tert.-butoxy group by methods known per se, i.e., by concentrated hydrochloric acid, producing 1$\beta$-hydroxy-5-oxo-7a$\beta$-methyl-5,6,7,7a-tetrahydroindan-4-carboxylic acid, m.p. 106°–108° C (decomp.). If the starting product is a 1$\beta$-acyloxy derivative of II the acylation follows methods known per se, i.e., with the anhydride of a hydrocarbon carboxylic acid, preferably acetic acid anhydride, in acetic acid and in the present of p-toluenesulfonic acid.

The etherification of the 1$\beta$-hydroxy group also is by methods known per se.

The 1,5-dioxo-7a$\beta$-methyl-5,6,7,7a-tetrahydroiandan-4-carboxylic acid (m.p. 57°–75° C under decomposition) is prepared from the corresponding 1$\beta$-hydroxy compound by oxidation, i.e., by chromic acid in acetone and in the present of sulfuric acid (Jone's reagent).

The katalization of the 1-oxo-group also is by methods known per se.

Starting products of formula II wherein R is ethyl are prepared from 1$\beta$-tert.-butoxy-5-oxo-7a$\beta$-ethyl-5,6,7,7a-tetrahydroindan-4-carboxylic acid (prepared analogously as described in DOS No. 1,949,800 for the corresponding 7a$\beta$-methyl compound) by the methods as described above for the compounds of formula II wherein R is methyl.

Compounds of formula II wherein $n$ is 2 are prepared by methods known per se and as mentioned above.

EXAMPLE 1

Preparation of trans-1$\beta$-tert.-Butoxy-5-oxo-7a$\beta$-methyl-3a$\alpha$, 4$\beta$,5,6,7,7a-hexahydroindan-4$\alpha$-carboxylic Acid a. In accordance with the process of this invention:

1.332 g. of 1$\beta$-tert.-butoxy-5-oxo-7a$\beta$-methyl-5,6,7,7a-tetrahydroindan-4-carboxylic acid (5 millimoles) is combined in 10.6 ml. of distilled water with 5 ml. of 1N sodium hydroxide solution. Then, 0.2 g. of 10% palladium-barium sulfate catalyst is added to the solution, and the hydrogenation is carried out for 20 minutes at room temperature and under normal pressure (ambient).

After termination of the hydrogenation, the catalyst is filtered off, the filtrate is acidified under ice cooling with 5.0 ml. of 1N hydrochloric acid, and the mixture is extracted with ether. The ether phase is washed with water, dried over sodium sulfate, and concentrated under vacuum, thus obtaining 1.35 g. of a crude product consisting, in accordance with analysis by gas chromatography, of 95.6% trans- and 3.9% cis-1$\beta$-tert.-butoxy-5-oxo-7a$\beta$-methyl-3a, 4,5,6,7,7a-hexahydroindan-4-carboxylic acid.

By conducting this hydrogenation at 0° C. rather than at room temperature, 1.38 g. of a crude product is obtained consisting of 97.6% trans- and 1.8% cis-1$\beta$-tert.-butoxy-5-oxo-7a$\beta$-methyl-3a,4,5,6,7,7a-hexahydroindan-4-carboxylic acid.

b. In accordance with the conventional method:

1.332 g. of 1$\beta$-tert.-butoxy-5-oxo-7a$\beta$-methyl-5,6,7,7a-tetrahydroindan-4-carboxylic acid is combined with 10.6 ml. of methanol and 0.2 g. of 10% palladium-barium sulfate catalyst, cooled to 0° C., and hydrogenated for 45 minutes under normal pressure at 0° C.

Then, the catalyst is filtered off, the filtrate is concentrated to dryness under vacuum, and the product is 1.38 g. of a crude substance consisting, according to analysis by gas chromatography, of 83.4% trans- and 15.8% cis-1$\beta$-tert.-butoxy-5-oxo-7a$\beta$-methyl-3a,4,5,6,7,7a-hexahydroindan-4-carboxylic acid.

EXAMPLE 2

Preparation of 1$\beta$-Hydroxy-5-oxo-7a$\beta$-methyl-3a$\alpha$, 4$\beta$,5,6,7,7a-hexahydroindan-4$\alpha$-carboxylic Acid a. According to the process of the present invention:

1.05 g. of 1$\beta$-hydroxy-5-oxo-7a$\beta$-methyl-5,6,7,7a-tetrahydroindan-4-carboxylic acid (5 millimoles) is combined with 10.6 ml. of distilled water and 5.0 ml. of 1N sodium hydroxide solution. Thereafter, 0.2 g. of 10% palladium-barium sulfate catalyst is added to the solution, and the latter is hydrogenated for 15 minutes at room temperature under normal pressure.

After the hydrogenation is terminated, the catalyst is filtered off, the filtrate is acidified under ice cooling with 5 ml. of 1N hydrochloric acid, and extracted with ethyl acetate. The extract is washed with water containing sodium chloride, dried over sodium sulfate, and concentrated under vacuum, thus obtaining 1.07 g. of a crude product consisting, according to gas-chromatographical analysis, of 95.5% trans- and 2.4% cis-1β-hydroxy-5-oxo-7aβ-methyl-3a,4,5,6,7,7a-hexahydroindan-4-carboxylic acid.

b. According to the conventional process:

1.05 g. of 1β-hydroxy-5-oxo-7aβ-methyl-5,6,7,7a-tetrahydroindan-4-carboxylic acid is combined with 10.7 ml. of methanol and 0.2 g. of 10% palladium-barium sulfate catalyst and hydrogenated for 10 minutes at 0° C. under normal pressure.

Then, the catalyst is filtered off, and the filtrate is concentrated under vacuum, thus obtaining 1.08 g. of a crude product consisting, as found by gas-chromatographical analysis, of 87.4% trans- and 12.6% cis-1β-hydroxy-5-oxo-7aβ-methyl-3a,4,5,6,7,7a-hexahydroindan-4-carboxylic acid.

EXAMPLE 3

Preparation of 1,5-Dioxo-7aβ-methyl-3aα,4β,5,6,7,7a-hexahydroindan-4α-carboxylic Acid a. In accordance with the process of this invention:

1.04 g. of 1,5-dioxo-7aβ-methyl-5,6,7,7a-tetrahydroindan-4-carboxylic acid (5 millimoles) is combined with 10.6 ml. of distilled water and 5.0 ml. of 1N sodium hydroxide solution. Then, 0.2 g. of 10% palladium-barium sulfate catalyst is added to the solution, and the latter is hydrogenated for 10 minutes at room temperature under normal pressure.

Thereafter, the catalyst is filtered off, the filtrate is cooled to about 0° C., acidified with 5.0 ml. of 1N hydrochloric acid, and extracted with methylene chloride. The methylene chloride phase is washed with water containing sodium chloride, dried over sodium sulfate, and concentrated under vacuum, thus obtaining 1.02 g. of a crude product which, according to analysis by gas chromatography, consists of 70.5% trans- and 19.4% cis-1,5-dioxo-7aβ-methyl-3a,4,5,6,7,7a-hexahydroindan-4-carboxylic acid.

b. In accordance with the conventional process:

1.04 g. of 1,5-dioxo-7aβ-methyl-5,6,7,7a-tetrahydroindan-4-carboxylic acid is combined with 10.7 ml. of methanol and 0.2 g. of 10% palladium-barium sulfate catalyst and hydrogenated for 6 minutes at 0° C. under normal pressure.

Thereafter, the catalyst is filtered off and the filtrate concentrated under vacuum, thus obtaining 1.09 g. of a crude product consisting, according to analysis by gas chromatography, of 52.4% trans- and 29.1% cis-1,5-dioxo-7aβ-methyl-3a,4,5,6,7,7a-hexahydroindan-4-carboxylic acid.

EXAMPLE 4

26.6 g. of 1β-tert.-butoxy-5-oxo-7aβ-methyl-5,6,7,7a-tetrahydroindan-4-carboxylic acid is combined with 150 ml. of twice distilled water and 100 ml. of 1N sodium hydroxide. The solution is adjusted to pH 5.5 with 10% aqueous acetic acid, filtered, and brought to a volume of 1000 ml.

100 ml. of this solution is hydrogenated in the presence of 500 mg. of platinum black at 0° C. for 90 minutes.

The reaction mixture is worked up as described in Example 1(a), thus obtaining 2.6 g. of a crude product consisting, according to analysis by gas chromatography, of 97.5% trans- and 0.9% cis-1β-tert.-butoxy-5-oxo-7aβ-methyl-3a,4,5,6,7,7a-hexahydroindan-4-carboxylic acid.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of a bicycloalkane derivative of the formula

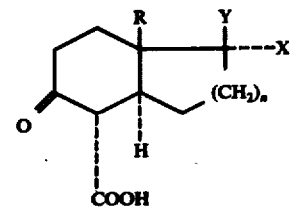

wherein n is the integer 1 or 2; R is methyl or ethyl, and X and Y collectively are oxo, alkylenedioxy of 2–6 carbon atoms inclusive and 2–3 bridging carbon atoms or phenylenedioxy or X is a hydrogen atom and Y is hydroxy, alkoxy of 1–6 carbon atoms, inclusive, or acyloxy wherein acyl is the acyl radical of a hydrocarbon carboxylic acid of 1–8 carbon atoms, inclusive, by the hydrogenation of a compound of the formula

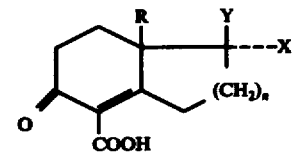

wherein n, R, X and Y have the values given above, with hydrogen and a palladium-, platinum-, or rhodium-containing hydrogenation catalyst, the improvement which comprises hydrogenating the starting compound as its alkali metal salt in water at about 0° C.

2. A process according to claim 1, wherein the reaction mixture is thereafter acidified and the thus-produced free acid is isolated therefrom.

3. A process according to claim 1, wherein n is 1, R is methyl, X and Y are oxo and the alkali metal salt is the sodium salt.

4. A process according to claim 1, wherein n is 1, R is methyl, Y is alkoxy of 1–6 carbon atoms, inclusive, and the alkali metal salt is the sodium salt.

5. A process according to claim 4, wherein Y is t-butoxy.

6. A process according to claim 1 wherein prior to the hydrogenation a solution of the starting free acid in the hydrogenation solvent is formed by reaction with 0.9–0.1 equivalents of sodium or potassium hydroxide and after the hydrogenation, the reaction mixture is thereafter acidified and the thus-produced free acid is isolated therefrom.

* * * * *